(12) United States Patent
Case

(10) Patent No.: US 9,797,830 B2
(45) Date of Patent: Oct. 24, 2017

(54) BIODIESEL DETECTOR

(71) Applicant: Emcee Electronics, Inc., Venice, FL (US)

(72) Inventor: Ryan Matthew Case, Sarasota, FL (US)

(73) Assignee: EMCEE ELECTRONICS, INC., Venice, FL (US)

( * ) Notice: Subject to any disclaimer, the term of this patent is extended or adjusted under 35 U.S.C. 154(b) by 0 days.

(21) Appl. No.: 14/936,737

(22) Filed: Nov. 10, 2015

(65) Prior Publication Data

US 2016/0139040 A1    May 19, 2016

Related U.S. Application Data

(60) Provisional application No. 62/079,129, filed on Nov. 13, 2014.

(51) Int. Cl.
*G01N 21/3577* (2014.01)
*G01N 21/31* (2006.01)
(Continued)

(52) U.S. Cl.
CPC ..... *G01N 21/3577* (2013.01); *G01N 21/3103* (2013.01); *G01N 21/359* (2013.01);
(Continued)

(58) Field of Classification Search
CPC ............ G01N 21/3577; G01N 21/359; G01N 2021/3595
(Continued)

(56) References Cited

U.S. PATENT DOCUMENTS 8,586,365 B2    11/2013    Wells et al.
9,329,085 B2 *   5/2016    Kotidis ................. G01J 3/4338
(Continued)

FOREIGN PATENT DOCUMENTS

DE          10349893 B3    4/2005
GB          2261285 A  *  11/1992  ............. G01N 21/03
(Continued)

OTHER PUBLICATIONS

"FT-IR Sampling Parameters for Exhaust Gas Measurements", Technical Note: 50650, Thermo Scientific (2007), p. 1-3, available at https://tools.thermofisher.com/content/sfs/brochures/D10071~.pdf.*

(Continued)

*Primary Examiner* — Kenneth J Malkowski
(74) *Attorney, Agent, or Firm* — William A. Ziehler; Shumaker, Loop & Kendrick, LLC

(57) ABSTRACT

A device and method of use are provided for measuring the concentration of fatty acid methyl ester (FAME) in jet fuel to a limit of detection of 1 ppm. The device measures concentration of FAME in jet fuel via Fourier transform infrared spectroscopy (FTIR) with a spectral resolution of 1 $cm^{-1}$. The device can use an infrared light emitting diode (IR LED) and mercury cadmium telluride (MCT) detector in which the spectral output of the IR LED and the spectral response of the MCT detector is centered on the spectral absorbance of an ester bond, a defining spectral characteristic of FAME. Other IR LEDs with differing spectral outputs can be used to measure the presence and/or concentration of different analytes in different fluids.

16 Claims, 3 Drawing Sheets

(51) Int. Cl.
*G01N 21/359* (2014.01)
*G01N 21/35* (2014.01)

(52) U.S. Cl.
CPC ........... *G01N 2021/3595* (2013.01); *G01N 2201/0612* (2013.01); *G01N 2201/0621* (2013.01)

(58) Field of Classification Search
USPC ....................................................... 356/440
See application file for complete search history.

(56) References Cited

U.S. PATENT DOCUMENTS

| | | | |
|---|---|---|---|
| 2009/0316139 | A1 | 12/2009 | Shrestha et al. |
| 2010/0116991 | A1* | 5/2010 | Saul .................. G01N 21/3577 250/339.07 |
| 2011/0255745 | A1* | 10/2011 | Hodder ............... G01N 21/359 382/103 |
| 2012/0261567 | A1 | 10/2012 | Voorhees et al. |
| 2013/0265566 | A1* | 10/2013 | Smith ...................... G01J 3/10 356/39 |
| 2014/0320861 | A1* | 10/2014 | van den Engh ....... G01N 21/85 356/440 |

FOREIGN PATENT DOCUMENTS

| | | |
|---|---|---|
| WO | 2009137122 A2 | 11/2009 |
| WO | 2011075420 A1 | 6/2011 |

OTHER PUBLICATIONS

Block Engineering, "MCT IR Detector Module: Spectral Acquisition Detection", http://www.blockeng.com/products/mct.html, 2013, Marlborough, MA, USA.

Kole, Matthew R. et al, Illinois University, "Discrete Frequency Infrared Microspectroscopy and Imaging with a Tunable Quantum Cascade Laser", Analytical Chemistry, Oct. 31, 2012, 84, pp. 10366-10372, Urbana, Illinois, USA.

Eide, Ingvar, et al., Statoil Research Center, "Detection of 5 ppm Fatty Acid Methyl Ester (FAME) in Jet Fuel Using Electrospray Ionization Mass Spectrometry and Chemometrics", ACS Publications, May 28, 2010, 24 (6), pp. 3661-3664, Trondheim, Norway.

Lissitsyna, Kristina, et al. "Determination of Trace Levels of Fatty Acid Methyl Esters in Aviation Fuel by GC x GC-FID and Comparison with the Reference GC-MS Method" Springer, Nov. 2012, vol. 75, Issue 21-22, pp. 1319-1325.

* cited by examiner

BIODIESEL DETECTOR

CROSS-REFERENCE TO RELATED APPLICATIONS

This application claims the benefit of U.S. Provisional Application No. 62/079,129, filed on Nov. 13, 2014. The entire disclosure of the above application is incorporated herein by reference.

FIELD

The present technology relates to detecting and measuring an analyte in a fluid, such as the detection and measurement of biodiesel in various fluids, including jet fuel, petroleum diesel fuel, and gasoline, and includes detection of trace quantities of the analyte in the parts per million range or lower.

INTRODUCTION

This section provides background information related to the present disclosure which is not necessarily prior art.

Biodiesel includes mono-alkyl esters of long chain fatty acids derived from vegetable oils or animal fats. Fatty acids in oils and fats are typically present as triglycerides, being esters formed with glycerol. Biodiesel production includes transesterification of the triglycerides with monoalcohols, such as methanol or ethanol, in the presence of a catalyst. Methanol is commonly used to produce methyl esters, commonly referred to as fatty acid methyl ester (FAME), as methanol is one of the least expensive alcohols. The resulting biodiesel is typically a mixture of fatty acid esters, where the types and relative amounts of fatty acid esters in the mixture depend on the feedstock used. After this processing, the combustion characteristics of the biodiesel are more like those of petroleum diesel.

Biodiesel contains essentially no aromatic compounds. Aromatic (or aryl) compounds are a large class of unsaturated cyclic hydrocarbons containing one or more rings. In particular, aromatic structures contain a number of double bonds that interact with each other according to certain rules. Benzene is a typical aromatic compound, which has a 6-carbon ring containing three delocalized double bonds.

Petroleum diesel fuel is distilled from crude petroleum and includes primarily aliphatic alkanes (primarily paraffins) and aromatic hydrocarbons, including naphthalenes and alkylbenzenes. The aliphatic alkanes constitute the about three-quarters of the distillate fraction and average about 12 carbon atoms in length. The distillate remainder of aromatic hydrocarbons can serve as an identifying characteristic of petroleum diesel.

Biodiesel and petroleum diesel have many common features. Biodiesel is typically suitable for use in diesel engines without any engine modification. However, there are some important differences between the two fuels. Because of these differences, many engine manufacturers recommend limiting the amount of biodiesel blended with petroleum diesel fuel.

The blend level (biodiesel percentage in a biodiesel-petroleum diesel mixture) determines certain characteristics of the blended fuel. Blends of biodiesel and petroleum diesel are designated by the letter "B" and a number denoting the biodiesel percentage within the blend, i.e., B5, B10, etc. Using biodiesel blends having higher biodiesel levels than recommended may compromise engine performance. Lower blend levels may reduce expected benefits, such as fuel lubricity and lower tail pipe emissions of unburned hydrocarbons, carbon monoxide, particulate matter, nitrogen oxides, sulfates, polycyclic aromatic hydrocarbons (PAHs), and nitrated PAHs. In addition, biodiesel cloud and pour points are usually higher than those of petroleum diesel fuel. The cloud point is the temperature at which the fuel becomes hazy or cloudy due to wax crystal formation. The pour point is the lowest temperature at which an oil will flow. As the percentage of biodiesel increases (i.e., a higher blend level) the fuel blend consequently becomes unsuitable or difficult to use in cold weather conditions. Furthermore, engine injection timing can only be adjusted to a certain extent based on the blend level in order to improve engine emissions and performance.

The presence of biodiesel in certain fluids, even at low concentrations, can compromise performance in certain engines or can interfere with certain processes. It can be important to ascertain the presence and/or the amount of biodiesel in such applications. Where the presence of biodiesel can render the fluid unsuitable for its intended use, it would be advantageous to determine whether the fluid is contaminated with biodiesel. For example, the transport and storage of various fluids, including biodiesel, petroleum diesel, gasoline, jet fuel, and components thereof, provides opportunities for undesired mixing of fluids, including contamination by residual amounts of one or more fluids from prior use of transport or storage containers, pipelines, or hoses, for example.

Accordingly, there is a need to detect an analyte, such as biodiesel, in a fluid at the level of parts per million or better in a short amount of time; e.g., from seconds to minutes.

SUMMARY

The present technology includes devices, systems, and processes that relate to detecting a concentration of an analyte in various fluids, including the detection of biodiesel in fluids such as jet fuel, petroleum diesel fuel, and gasoline.

A device or system for detection of an analyte in a fluid includes an infrared light source, a detector, and fluid positioning means, such as a sample stage. The light source can include an infrared light emitting diode (IR LED) or a quantum cascade laser. The detector can include mercury cadmium telluride (MCT). Temperature of the detector and/or the infrared light source can also be controlled by a temperature control means, such as a cooling system, including a thermoelectric or Peltier system, a heat exchanger, and a pump. The fluid positioning means can be disposed intermediate the light source and the detector, where the fluid positioning means can be configured to allow one or more fluid samples to pass therethrough, including one or more disposable containers of fluid samples to be placed thereon or moved therethrough. The device or system can include electronics including a driver for the light source, signal processing means configured to transform a detector voltage to a readout for a concentration value of the analyte, temperature control of the light source, a detector to maintain uniformity in spectral output of the light source and spectral response of the detector, and one or more sensors to monitor concentration of water vapor and oxygen to determine the effectiveness of nitrogen purging of the device. Additional optical components can include one or more various mirrors and apertures to focus and collimate light emitted from the light source.

Methods of detecting an analyte in a fluid are also provided, including methods of using the devices and systems as described herein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 graphically depicts a butterfly for N=2 in relation to use of Fourier transform infrared spectroscopy (FTIR) for detecting biodiesel according to the present technology.

FIG. 2 graphically depicts a butterfly for N=4 in relation to use of FTIR for detecting biodiesel according to the present technology.

DETAILED DESCRIPTION

Figure 1:
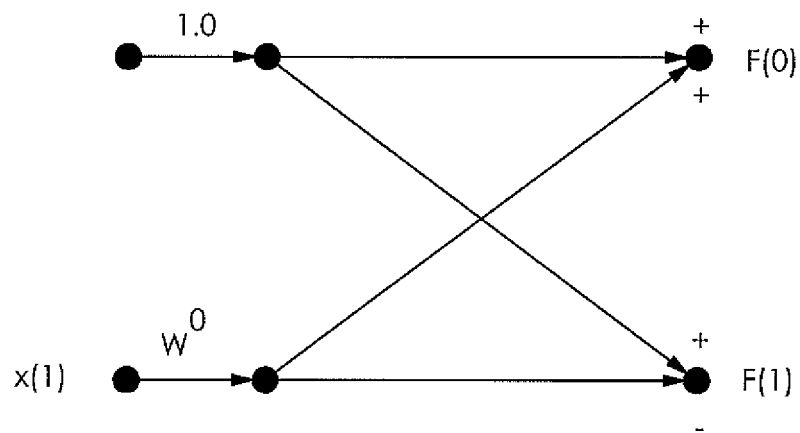

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology can detect an analyte in various fluids. As one example, biodiesel can be detected in various fluids, including jet fuel, petroleum diesel fuel, and gasoline. Detection can include determining the presence of trace amounts of the analyte and can include determining a concentration of the analyte, including the measurement of analyte concentrations on the order of parts per million (ppm), down to about 1 ppm or less. An device or system constructed according to the present technology can include an infrared light source, a detector, and a fluid positioning means, such as a sample stage to hold one or more fluid reservoirs or cuvettes. The device or system can be compact in dimension, can have a low profile (e.g., about the size of a breadbox), and can be portable or reversibly coupled to various fluid containment, pumping, or handling systems. The present technology can furthermore be used to measure other analytes in other fluids, including detection of ethanol in jet fuel, biodiesel, petroleum diesel, and gasoline, as well as detection of gasoline in biodiesel and petroleum diesel. Various ways of detecting various analytes in fluids are provided, including various methods of using the devices and systems described herein.

The devices and methods of using such devices described herein can measure the concentration of fatty acid methyl ester (FAME) in jet fuel at the level of ppm, where certain embodiments include a detection limit down to at least 1 ppm. The device measures the presence or concentration of FAME in jet fuel via Fourier transform infrared spectroscopy (FTIR) with a spectral resolution of 1 $cm^{-1}$. The device can use an infrared light emitting diode OR LED) or a quantum cascade laser and a detector such as a mercury cadmium telluride (MCT) detector in which the spectral output of the IR LED and the spectral response of the detector is substantially centered on the spectral absorbance of an ester bond, a defining spectral characteristic of FAME. Other IR LEDs with differing spectral outputs can be used to measure the concentrations of different analytes in different fluids. The device can use a fluid positioning means configured to position the fluid so that a beam from the infrared light source passes through the fluid to be analyzed. The fluid positioning means can include various fluid reservoirs, such as disposable cuvettes in order to eliminate cross contamination between fluid samples. Furthermore, the device utilizes temperature control of the light source and the detector to maintain uniformity in the spectral output of the light source and the spectral response of the detector.

FTIR instruments can provide attenuation versus wavenumber as the output associated with a FTIR measurement. This output does not directly provide information on the concentration of a given analyte in a given fluid sample to be tested. As a result, an experienced chemist would need to interpret the result from the FTIR instrument and deduce the concentration of such analyte in the fluid based on a specific transformation. The present device performs this transformation and provides the concentration of the specified analyte in the fluid to the user. In particular, the present device can determine the analyte concentration down to 1 ppm, providing an advantageously sensitive means to determine the presence, and hence possible contamination, by a given analyte in a given fluid sample.

The fluid positioning means used to position the fluid sample for the device can include various types of reservoirs used for fluid containment, handling, and transferring of one or more fluid samples. For example, the device can be configured to load and unload a fluid sample into and out of the fluid positioning means using a pump or the fluid positioning means can be a portion of a tube or conduit through which the fluid sample passes. The fluid can be held or paused within the fluid positioning means or the fluid can flow through the fluid positioning means. Where the fluid is flowing through the fluid positioning means, the device can provide a real-time output of analyte concentration for the fluid flow. In certain embodiments, the fluid positioning means can be configured as a disposable cuvette, constructed with various windows, such as silicon windows, and can have a chemically inert housing. Windows of the cuvette can have an antireflection coating disposed thereon. Silicon windows can be used because silicon is transparent in the spectral window of interest; e.g., infrared light. Other fluid reservoirs include disposable and non-disposable containers or cuvettes having sodium chloride, potassium bromide, calcium fluoride, barium fluoride, or zinc selenide windows. Sodium chloride windows are transparent in the spectral window of interest, but they can be highly hydroscopic and may promote cross contamination from sample to sample. Having disposable cuvettes removes the cross contamination issue, which can be important in certain uses for the device to achieve detection limits on the order of parts per million, including down to 1 ppm.

The fluid positioning means can include a sample stage or can be removably coupled to a sample stage, where the sample stage can be configured for use with various fluid reservoirs having various volumes and/or shapes, including one or more adjustable sample stages to accommodate various shapes and sizes of disposable fluid reservoirs. The sample stage can be automated to advance one or more fluid reservoirs in a queue, placing each fluid reservoir to be measured within a measurement register for an appropriate time with respect to the light source and detector. The fluid sample can also be moved through the sample stage using a pump or other fluid handling device.

Measurement of biodiesel concentrations can include the use of Fourier transform infrared spectroscopy (FTIR), in which the light source can be a glowing blackbody source. The means of measuring concentrations of any substance within a sample can rest in the attenuation of the substance at any given wavelength. For example, an ester bond, which is present in biodiesel (e.g., FAME), has a predominant attenuation at a wavenumber of about 1745 $cm^{-1}$, corresponding to a wavelength of 5.73 µm; this feature separates FAME from jet fuel and petroleum diesel, and can be used for detecting biodiesel. For ethanol, corresponding wavenumbers for predominant attenuation are 3348 $cm^{-1}$ and 3633.3 $cm^{-1}$, corresponding to wavelengths of 2.99 µm and 2.75 µm, respectively. Gasoline contains a distinctive absorbance at a wavenumber of 3602.2 $cm^{-1}$, corresponding to a wavelength of 2.78 µm. Glowing blackbody sources emit very broad spectral bands and, as a result, the proportion of the intensity corresponding to the desired wavelength to total intensity from the source is very small.

Embodiments of the present technology include where the light source has one or more narrow spectral bands substantially centered on one or more desired wavelengths, so that the light beam can interact strongly with fluid samples to enhance the sensitivity of measuring biodiesel concentration. There are accordingly several considerations in the selection and use of a particular light source. For example, use of blackbody radiation as a light source presents two problems. First, a glowing blackbody source requires a filament at an elevated temperature (about 800° C. to 1000° C.), whereas typically other components of a detection device or system need to be maintained at or below room temperature. Second, a glowing blackbody source emits very broad spectral bands and consequently the proportion of the intensity corresponding to the desired wavelength to total intensity from the source is very small.

The present technology overcomes these issues by using an infrared light emitting diode (IR LED) or a quantum cascade laser as a light source. These light sources can produce a narrow spectral band substantially centered on a desired wavelength, so that a light beam therefrom interacts strongly with a sample to enhance the sensitivity of measuring biodiesel concentration. By "substantially centered," it is meant that the beam of light includes only a portion of the infrared spectrum, where the portion of the infrared spectrum includes a wavelength absorbable by the analyte as well as a longer infrared wavelength and a shorter infrared wavelength. In this way, a peak absorbance by the analyte can be determined, as well as a portion of the infrared spectrum on each side of the peak absorbance. In some embodiments, the portion of the infrared spectrum substantially centered on the wavelength absorbable by the analyte can include a range of wavelengths spanning anywhere from about 1,000 nm to about 3,000 nm, with about 500-1,500 nm of the range of wavelengths on either side of the wavelength absorbable by the analyte. For example, the ester bond present in biodiesel (e.g., FAME) has a predominant attenuation at a wavenumber of about 1745 $cm^{-1}$, which corresponds to a wavelength of about 5.73 µm. Accordingly, the portion of the infrared spectrum substantially centered on the wavelength of about 5.73 µm can include infrared wavelengths from about 4.23 µm to about 7.23 µm. IR LEDs can provide a portion or window of the IR spectrum in these ranges. In some embodiments, the portion of the infrared spectrum substantially centered on the wavelength absorbable by the analyte can include a range of wavelengths spanning anywhere from about 50 nm to about 150 nm, with about 25-75 nm of the range of wavelengths on either side of the wavelength absorbable by the analyte. For example, the portion of the infrared spectrum substantially centered on the wavelength of about 5.73 µm (for FAME) can include infrared wavelengths from about 5.655 µm to about 5.805 µm. A quantum cascade laser can provide a portion or window of the IR spectrum in these ranges. In some embodiments, the range of wavelengths can span anywhere from about 10 nm to about 50 nm, with about 5 nm to about 25 nm of the range of wavelengths on either side of the wavelength absorbable by the analyte. For example, the portion of the infrared spectrum substantially centered on the wavelength of about 5.73 μm (for FAME) can include infrared wavelengths from about 5.68 μm to about 5.78 μm. A quantum cascade laser can provide a portion or window of the IR spectrum in these ranges. It should be noted that wavelength values can be converted to wavenumber values, and vice versa, depending on the desired reporting and analysis.

Where an IR LED is used as the light source, the infrared LEDs can be tailored to emit radiation at a specified wavelength and can also have narrow spectral widths substantially centered on a wavelength absorbable by the analyte. The IR LED can produce high intensity light at target wavelengths and does not need to be heated to elevated temperatures, making IR LEDs suitable for use in the present devices. Where a quantum cascade laser is used as the light source, the quantum cascade laser can be tailored to emit radiation at a specified wavelength and can also have narrow spectral widths substantially centered on a wavelength absorbable by the analyte. The quantum cascade laser can be collimated at a comparatively high intensity.

The detector can include a mercury cadmium telluride (MCT) detector. MCT is also known as MerCad Telluride, MerCadTel, MerCaT, and cadmium mercury telluride (CMT). MCT is a narrow direct bandgap zincblende II-VI ternary alloy of CdTe and HgTe with a tunable bandgap spanning the shortwave infrared to the very long wave infrared regions. The amount of cadmium (Cd) in the alloy can be chosen so as to tune the optical absorption of the material to the desired infrared wavelength. CdTe is a semiconductor with a bandgap of approximately 1.5 eV at room temperature, HgTe is a semimetal, hence its bandgap energy is zero, where mixing these two substances can therefore provide any bandgap between 0 and 1.5 eV.

The temperature of the MCT detector can be controlled by a temperature control means in order to minimize thermal noise. The temperature control means can include a cooling system having a four-stage thermoelectric or Peltier system, a heat exchanger, and a compressor, which can drive a refrigeration system. In certain embodiments, the temperature control means can include a heat exchanger and a coolant loop to remove heat from the infrared light source and/or the detector. Where the light source includes one or more IR LEDs, which do not need to be heated, the MCT can be cooled more efficiently. For example, IR LEDs emitting between 2 μm to 7 μm and MCT detectors that need only thermoelectric cooling and that are sensitive to radiation between 2 μm to 7 μm can be used.

The present technology can include additional optical components, such as various lenses, collimators, mirrors, diffraction gratings, and slits to manage the beam of light emitted from the light source and to further isolate the desired wavelengths substantially centered on a wavelength absorbable by the analyte.

The device or system can further include various processor, sensor, and control components, including a driver for the light source (e.g., laser) and a processor configured to transform an electric signal from the detector (e.g., a voltage) to an indication or readout for the presence of the analyte in the fluid and/or for reporting a concentration value of the analyte in the fluid. FTIR analysis can be used to determine the concentration of the analyte in the fluid, where the concentration can be provided in parts per million. A computer readable medium, including a non-transient computer readable medium, can include a transformation process for FTIR analysis of the fluid.

As an example, the FTIR analysis can be tailored for the detection of the analyte according to the following transformation process:

Light leaving beam splitter:

$$I = |E|^2 = |E_1|^2 + |E_2|^2 + 2E_1 \cdot E_2 = |E_1|^2 + |E_2|^2 + 2|E_1||E_2|\cos(\theta)$$

$$|E_1|^2 = |E_2|^2 = I_0$$

Normal incidence, angular mismatch $\theta = k\,\delta$, so $$I(\delta) = 2I_0(1 + \cos(2\pi k\delta)) \text{ or } I(\delta) = 2I_0\left(1 + \cos\left(2\pi\frac{\delta}{\lambda}\right)\right)$$

For non-monochromatic light, $$I(\delta) = \int_{-\infty}^{\infty} 2A(k)(1+\cos(2\pi k\delta))\,dk = 4\int_0^{\infty} A(k)(1+\cos(2\pi k\delta))\,dk$$

for $A(-k) = A(k)$

When $\delta = 0$, $$I(0) = 4\int_0^{\infty} A(k)\,dk + 4\int_0^{\infty} A(k)\cos(2\pi k\delta)\,dk$$

$$I(0) = 8\int_0^{\infty} A(k)\,dk \Rightarrow \int_0^{\infty} A(k)\,dk = \frac{1}{8}I(0)$$

$$\frac{I(\delta)}{4} - \frac{I(0)}{8} = \int_0^{\infty} A(k)\cos(2\pi k\delta)\,dk = \frac{1}{4}\left(I(\delta) - \frac{1}{2}I(0)\right)$$

so that $$A(k) = \int_0^{\infty} \frac{1}{4}\left(I(\delta) - \frac{1}{2}I(0)\right)\cos(2\pi k\delta)\,d\delta \text{ or}$$

$$A(\lambda) = \int_0^{\infty} \frac{1}{4}\left(I(\delta) - \frac{1}{2}I(0)\right)\cos\left(2\pi\frac{\delta}{\lambda}\right)d\delta \text{ Or}$$

$$A(k) = Re\left(\int_0^{\infty} \frac{1}{4}\left(I(\delta) - \frac{1}{2}I(0)\right)e^{-i2\pi k\delta}\,d\delta\right) \text{ or}$$

$$A(\lambda) = Re\left(\int_0^{\infty} \frac{1}{4}\left(I(\delta) - \frac{1}{2}I(0)\right)e^{-i2\pi\frac{\delta}{\lambda}}\,d\delta\right)$$

Since this operation treats the data as if it were periodic, we evaluate the Discrete Fourier Transform, as sampling at N discrete points $\delta = n\Delta$ (so that the distance between sampling mints is $\Delta$):

$$A[k] = \sum_{n=0}^{N-1} \frac{1}{4}\left(I[n\Delta] - \frac{1}{2}I[0]\right)e^{i2\pi\Delta nk}$$

or $$A[\lambda] = \sum_{n=0}^{N-1} \frac{1}{4}\left(I[n\Delta] - \frac{1}{2}I[0]\right)e^{-i2\pi n\frac{\Delta}{\lambda}}$$

This can be written in matrix form as $$\begin{pmatrix} A[0] \\ A[1] \\ \vdots \\ A[N-1] \end{pmatrix} = \frac{1}{4} \begin{pmatrix} 1 & 1 & 1 & 1 & \cdots & 1 \\ 1 & W & W^2 & W^3 & \cdots & W^{N-1} \\ 1 & W^2 & W^4 & W^6 & \cdots & W^{2(N-1)} \\ 1 & W^3 & W^6 & W^9 & \cdots & W^{3(N-1)} \\ \vdots & \vdots & \vdots & \vdots & \ddots & \vdots \\ 1 & W^{N-1} & W^{2(N-1)} & W^{3(N-1)} & \cdots & W^{(N-1)^2} \end{pmatrix} \begin{pmatrix} \frac{1}{2}I[0] \\ I[1]-\frac{1}{2}I[0] \\ I[2]-\frac{1}{2}I[0] \\ \vdots \\ I[N-2]-\frac{1}{2}I[0] \\ I[N-1]-\frac{1}{2}I[0] \end{pmatrix}$$

with $$W = e^{-i\left(\frac{2\pi}{N}\right)}$$

so that $W^N=1$; note that the I's index as multiples of $\Delta$ and the k's index as multiples of $$\frac{1}{N\Delta}.$$

Let $$\begin{pmatrix} x[0] \\ x[1] \\ x[2] \\ \vdots \\ x[N-2] \\ x[N-1] \end{pmatrix} = \frac{1}{4} \begin{pmatrix} \frac{1}{2}I[0] \\ I[1]-\frac{1}{2}I[0] \\ I[2]-\frac{1}{2}I[0] \\ \vdots \\ I[N-2]-\frac{1}{2}I[0] \\ I[N-1]-\frac{1}{2}I[0] \end{pmatrix}$$

(note that the x's index as multiples of $\Delta$) so that $$\begin{pmatrix} A[0] \\ A[1] \\ \vdots \\ A[N-1] \end{pmatrix} = \begin{pmatrix} 1 & 1 & 1 & 1 & \cdots & 1 \\ 1 & W & W^2 & W^3 & \cdots & W^{N-1} \\ 1 & W^2 & W^4 & W^6 & \cdots & W^{2(N-1)} \\ 1 & W^3 & W^6 & W^9 & \cdots & W^{3(N-1)} \\ \vdots & \vdots & \vdots & \vdots & \ddots & \vdots \\ 1 & W^{N-1} & W^{2(N-1)} & W^{3(N-1)} & \cdots & W^{(N-1)^2} \end{pmatrix} \begin{pmatrix} x[0] \\ x[1] \\ x[2] \\ \vdots \\ x[N-2] \\ x[N-1] \end{pmatrix}$$

Use a FFT routine to determine A[n]'s:
Now break the series up into its even and odd terms:

$$A[k] = \sum_{n=0}^{N-1} x[n]W^{nk} = \sum_{n=0}^{\frac{N}{2}-1} x[2n]W^{2nk} + \sum_{n=0}^{\frac{N}{2}-1} x[2n+1]W^{(2n+1)k}$$

$$A[k] = \sum_{n=0}^{\frac{N}{2}-1} x[2n]W^{2nk} + \sum_{n=0}^{\frac{N}{2}-1} x[2n+1]W^{2nk}W^k$$

$$A[k] = \sum_{n=0}^{\frac{N}{2}-1} x[2n]W^{2nk} + W^k \sum_{n=0}^{\frac{N}{2}-1} x[2n+1]W^{2nk}$$

$$A[k] = E[k] + W^k O[k] \text{ where } E[k] = \sum_{n=0}^{\frac{N}{2}-1} x[2n]W^{2nk} \text{ and}$$

$$O[k] = \sum_{n=0}^{\frac{N}{2}-1} x[2n+1]W^{2nk}$$

Note that $$W^k = e^{-i\frac{2\pi k}{N}} \Rightarrow W^{2k} = e^{-i\frac{2\pi 2k}{N}} = e^{-i\frac{2\pi k}{N/2}}$$

$$W^{k+\frac{N}{2}} = e^{-i\frac{2\pi k}{N}-i\pi} = -e^{-i\frac{2\pi k}{N}} = -W^k \text{ so that}$$

$$E\left[k+\frac{N}{2}\right] = \sum_{n=0}^{\frac{N}{2}-1} x[2n]W^{2n\left(k+\frac{N}{2}\right)} = E[k] \text{ and}$$

$$O\left[k+\frac{N}{2}\right] = O[k]$$

Thus $$A[k] = E[k] + W^k O[k] \text{ and } A\left[k+\frac{N}{2}\right] = E[k] - W^k O[k]$$

TABLE 1

| | 2-point FFT |
|---|---|
| E[0] | $E[0] = \sum_{n=0}^{\frac{2}{2}-1} x[2n]W^{2n(0)} = x[0]W^0 = x[0]$ |
| O[0] | $O[0] = \sum_{n=0}^{\frac{2}{2}-1} x[2n+1]W^{2n(0)} = x[1]W^0 = x[1]$ |
| A[0] | $A[0] = E[0] + W^0 O[0] = x[0] + x[1]$ |
| A[1] | $A\left[0+\frac{2}{2}\right] = E[0] - W^0 O[0] = x[0] - x[1]$ |

FIG. 1 illustrates a butterfly for N=2.

TABLE 2

| | 4-point FFT |
|---|---|
| E[0] | $E[0] = \sum_{n=0}^{\frac{4}{2}-1} x[2n]W^{2n(0)} = x[0]W^0 + x[2]W^{2(1)(0)} = x[0] + x[2]$ |

TABLE 2-continued 4-point FFT

E[1]
$$E[1] = \sum_{n=0}^{\frac{4}{2}-1} x[2n]W^{2n(1)} = x[0]W^0 + x[2]W^{2(1)(1)} =$$
$$x[0] + W^2 x[2] = x[0] - x[2]$$

O[0]
$$O[0] = \sum_{n=0}^{\frac{4}{2}-1} x[2n+1]W^{2n(0)} = x[1]W^0 + x[3]W^{2(1)(0)} = x[1] + x[3]$$

O[1]
$$O[1] = \sum_{n=0}^{\frac{4}{2}-1} x[2n+1]W^{2n(1)} = x[1]W^0 + x[3]W^{2(1)(1)} =$$
$$x[1] + W^2 x[3] = x[1] - x[3]$$

A[0]   $A[0] = E[0] + W^0 O[0] = x[0] + x[2] + x[1] + x[3]$
A[1]   $A[1] = E[1] + W^1 O[1] = x[0] - x[2] + W(x[1] - x[3])$

A[2]
$$A\left[0 + \frac{4}{2}\right] = E[0] - W^0\ O[0] = x[0] + x[2] - x[1] - x[3]$$

A[3]
$$A\left[1 + \frac{4}{2}\right] = E[1] - W^1\ O[1] = x[0] - x[2] - W(x[1] - x[3])$$

Figure 2:
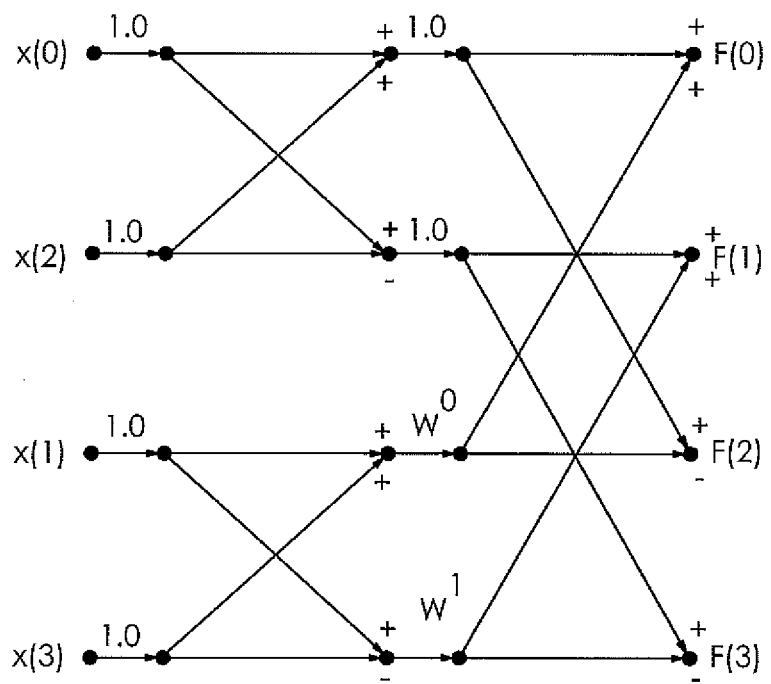

FIG. 2 illustrates a butterfly for N=4.
Once the A[k]'s are determined:
  The k's index as multiples of $$\frac{1}{N\Delta};$$

i.e., $$k = 0, \frac{1}{N\Delta}, \frac{2}{N\Delta}, \ldots, \frac{1}{2\Delta}.$$

The list of A[k]'s is one-half the length of the list of x[n]'s, as the second half of the A[k]'s are just the complex conjugates of the first half of the A[k]'s.
  The FFT magnitudes correspond to the spectrum of interest. These follow $$Mag(A[0]) = \frac{abs(A[0])}{N} \quad \text{for } k = 0$$

$$Mag(A[k]) = \frac{2abs(A[0])}{N} \quad \text{for } k = \frac{1}{N\Delta}, \frac{2}{N\Delta}, \ldots, \frac{N/2-1}{N\Delta}$$

$$Mag(A[k]) = \frac{abs(A[k])}{N} \quad \text{for } k = \frac{1}{2\Delta}$$

Indication of the analyte, including the presence and concentration of the analyte, can be determined using the Fourier Transform of the data obtained from the detector. The data from the detector can be further transformed as follows in order to quantify absorbance as follows:

$$\text{absorbance } a(x) = \ln\left(\frac{y_{no\ sample}}{y}\right),$$

where y corresponds to the Fourier Transformed data, and $y_{no\ sample}$ corresponds to the Fourier Transformed data associated with no sample in sample position. The absorbance data, including n data points, is put through a cubic spline interpolation to generate a piecewise continuous curve, consisting of a set of n−1 cubic equations joining the n absorbance data points $$a(x) = \begin{cases} d_{0,0} + d_{0,1}x + d_{0,2}x^2 + d_{0,3}x^3 & x_0 \leq x \leq x_1 \\ d_{1,0} + d_{1,1}x + d_{1,2}x^2 + d_{1,3}x^3 & x_1 \leq x \leq x_2 \\ M & M \\ d_{n-2,0} + d_{n-2,1}x + d_{n-2,2}x^2 + d_{n-2,3}x^3 & x_{n-2} \leq x \leq x_{n-1} \end{cases}$$

where $x_0, x_1, \ldots, x_{n-1}$ are the n absorbance points and $d_{i,j}$ are the coefficients of the cubic equations interpolating between each absorbance point. From this, the area of the peak of interest A is found by integrating the piecewise continuous curve over the wavenumber interval of interest:

$$A = \int_{x_{lower}}^{x_{upper}} (a(x) - a_{baseline}(x))dx$$

where a(x) is the absorbance at wavenumber x, and $a_{baseline}(x)$ is the baseline absorbance, associated with the line joining the absorbances at $x_{baseline\ 1}$ and $x_{baseline\ 2}$, $x_{lower}$ is the lower limit of integration, and $x_{upper}$ is the upper limit of integration. This area is compared against a linear regression calibration, in the form:

$$A = kc + b,$$

where A is the area from the procedure described, c is the concentration of analyte in appropriate units (for the case of FAME in jet fuel, the units for c would be ppm), and k and b are fitting constants from a set of calibration samples. To determine concentration, the linear regression line expression can be rearranged to:

$$c = \frac{A - b}{k}.$$

For example, in determining the concentration of FAME in jet fuel, $x_{baseline\ 1}$ is 1708 cm$^{-1}$ and $x_{baseline\ 2}$ is 1785 cm$^{-1}$, $x_{lower}$ is 1713 cm$^{-1}$, and $x_{upper}$ is 1784 cm$^{-1}$, respectively (following from ASTM D7806).

As described, the determination of the concentration of the analyte can include the process of cubic spline interpolation, as a means of determining interpolating curves between successive absorption points. The method of cubic spline interpolation is generally known in the art. However, one skilled in the art further recognizes that other ways of determining interpolating curves between successive absorption points can be used in the present methods.

In this way, the processor can employ these transformation processes to convert the electric signal from the detector to indicate presence of the analyte and/or determine a concentration value of the analyte. This allows a rapid determination of analyte concentration based on the portion of the infrared spectrum substantially centered on a wavelength absorbable by the analyte. The transformation process can change wave interference data into absorption for a given wavelength, including the wavelengths present in the portion of the infrared spectrum in the beam provided by the light source.

In some embodiments, a device constructed according to the present technology can be configured to have compact dimensions, making the device portable and suitable for field use. Dimensions can include about 18 inches in length, about 15 inches in depth, and about 15 inches in height. The sensitivity of the detector can be sub-nanowatt with a dynamic range factor of at least 100,000. The fluid reservoir can be disposable and can be about 1 mm long, have flat and parallel faces, and can hold around 20 mL of sample. The light source can emit on the order of tens of microwatts to milliwatts, and with optical components the emitted light can be focused to a cross section of about 6 mm×6 mm. The light moving through the fluid sample can have as little beam divergence and/or focusing as possible, so that the beam includes substantially parallel light rays.

Figure 3:
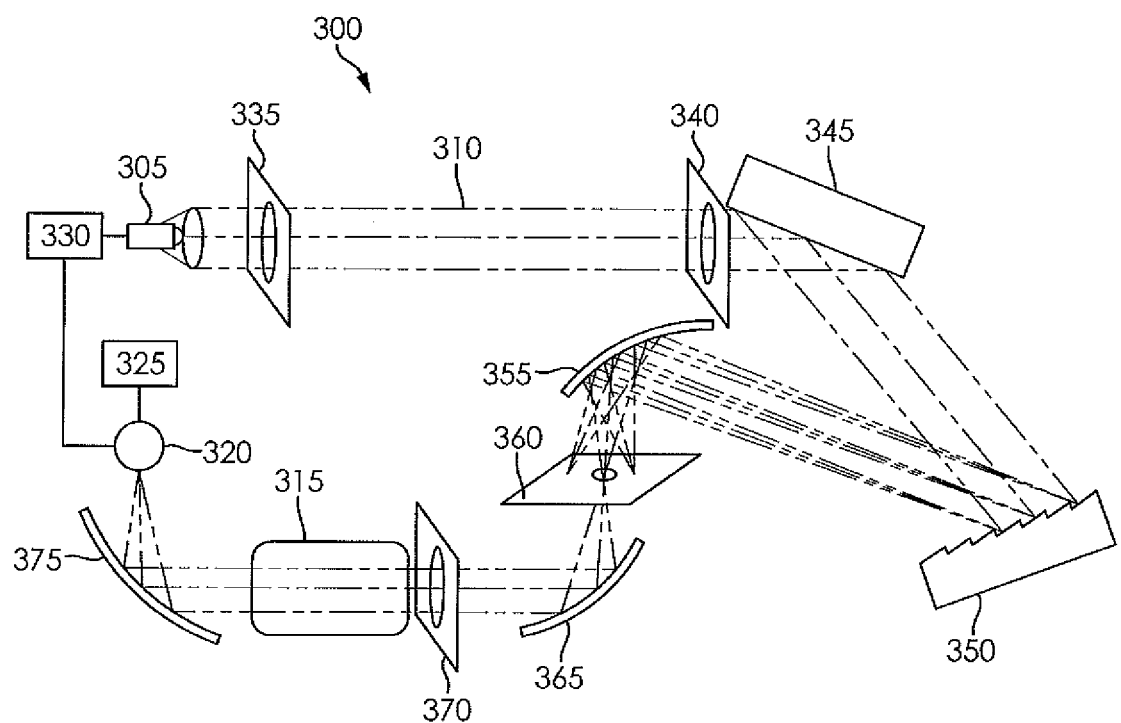
FIG. 3 depicts a schematic for an optical path-diffracting monochromator, where attenuation at one or more specified wavelengths provides a means to measure presence or concentration of a respective analyte.

FIG. 3 depicts an embodiment of a device 300 for detecting an analyte in a fluid constructed according to the present technology, where the device 300 is based on an optical path-diffracting monochromator arrangement, where attenuation at one or more specified wavelengths results in a means to measure concentration of a respective analyte in a fluid; e.g., FAME from biodiesel. The device 300 includes an infrared light source 305 (e.g., an IR LED or quantum cascade laser) that provides a beam 310 of light. The beam 310 includes a plurality of infrared wavelengths, where the infrared wavelengths include only a portion of the infrared spectrum, the portion being substantially centered on a wavelength absorbable by the analyte of interest. The beam 310 passes through a fluid positioning means 315, where the fluid positioning means 315 positions the fluid to be analyzed so that the beam 310 from the light source 305 passes through the fluid. A detector 320 (e.g., an MCT detector) receives the beam 310 from the infrared light source 305 after the beam 310 passes through the fluid as positioned by the fluid positioning means 315. The detector 320 is configured to translate infrared light into an electric signal. A processor 325 transforms the electric signal from the detector 320 to an indication of the analyte, where the indication can include a concentration value for the analyte in ppm. A temperature control means 330 controls a temperature of the infrared light source 305 and a temperature of the detector 320. In this way, the temperature control means 330 can maintain uniformity in the beam 310 provided by the infrared light source 305 and in the translation of the infrared light into the electric signal by the detector 320.

As shown, the device 300 in FIG. 3 provides an optical path-diffracting monochromator arrangement from the infrared light source 305 to the detector 320. This can be accomplished by use of a first collimating slit 335 and a second collimating slit 340 to collimate the beam 310 so that it includes parallel rays of infrared light. The beam 310 can then be redirected using a first mirror 345 to a diffraction grating 350, sent to a focusing mirror 355, and passed through an exiting slit 360 to provide substantially monochromatic infrared light. The beam 310 can then be sent to a second focusing mirror 365 and passed through a clean-up slit 370 prior to passing through the fluid held by the fluid positioning means 315. The beam 310 can then encounter a third focusing mirror 375 that directs the beam 310 to the detector 320. It should be noted that different arrangements, combinations, and sub-combinations of collimators, mirrors, diffraction grating(s), and/or slits can be employed to direct the beam 310 along a given path based on the dimensions and geometry of the device 300, the overall path-length and width of the beam 310, and the path-length and width of portions of the beam 310 between various collimators, mirrors, diffraction grating(s), and/or slits.

Figure 4:
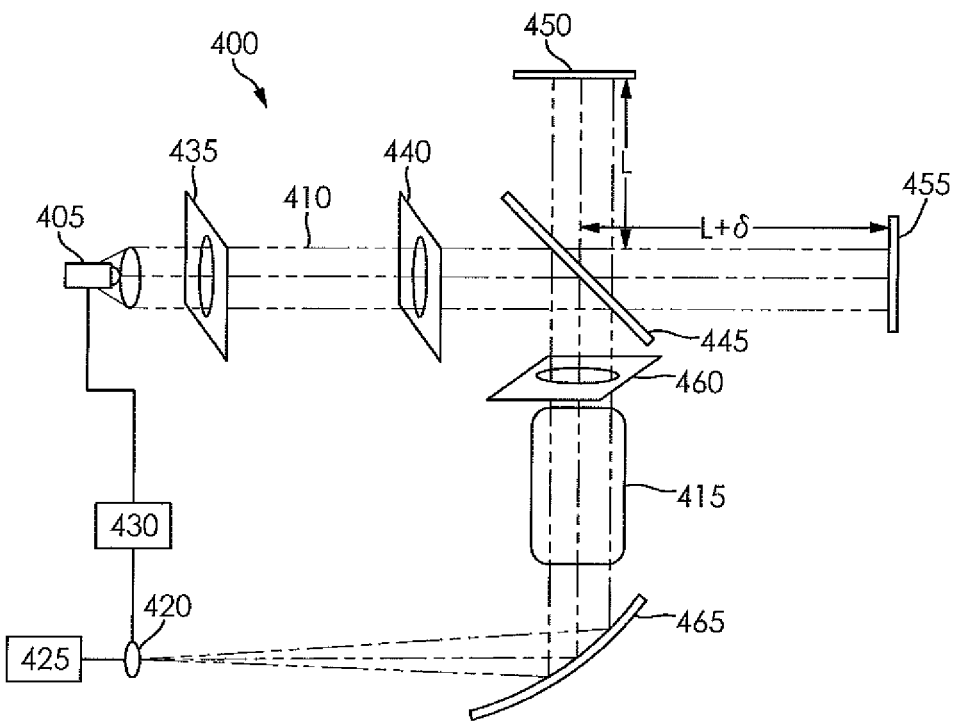
FIG. 4 depicts a schematic for an optical path for FTIR analysis of a sample from which the presence or concentration of a respective analyte can be ascertained.

FIG. 4 depicts an embodiment of another device 400 for detecting an analyte in a fluid constructed according to the present technology, where the device 400 employs an optical path for FTIR analysis of a fluid from which the concentration of the analyte can be ascertained. The device 400 includes an infrared light source 405 (e.g., an IR LED or quantum cascade laser) that provides a beam 410 of light. The beam 410 includes a plurality of infrared wavelengths, where the infrared wavelengths include only a portion of the infrared spectrum, the portion being substantially centered on a wavelength absorbable by the analyte of interest. The beam 410 passes through a fluid positioning means 415, where the fluid positioning means 415 positions the fluid to be analyzed so that the beam 410 from the light source 405 passes through the fluid. A detector 420 (e.g., an MCT detector) receives the beam 410 from the infrared light source 405 after the beam 410 passes through the fluid as positioned by the fluid positioning means 415. The detector 420 is configured to translate infrared light into an electric signal. A processor 425 transforms the electric signal from the detector 420 to an indication of the analyte, where the indication can include a concentration value for the analyte in ppm. A temperature control means 430 controls a temperature of the infrared light source 405 and a temperature of the detector 420. In this way, the temperature control means 430 can maintain uniformity in the beam 410 provided by the infrared light source 405 and in the translation of the infrared light into the electric signal by the detector 420.

As shown, the device 400 in FIG. 4 employs an optical path for FTIR analysis of the fluid from the infrared light source 405 to the detector 420. This can be accomplished by use of a first collimating slit 435 and a second collimating slit 440 to collimate the beam 410 so that it includes parallel rays of infrared light. The beam 410 can then be split by a beamsplitter 445 where a portion is directed to a fixed mirror 450 and a portion is directed to a moveable mirror 455. For example, the fixed mirror 450 can be positioned at a fixed distance (L) from the beamsplitter 445 and the moveable mirror 455 can be positioned at an adjustable distance (L δ) from the beam splitter 445. The split portions of the beam 410 can be sent through a clean-up slit 460 and passed through the fluid held by the fluid positioning means 415. The beam 410 can then encounter a focusing mirror 465 that directs the beam 410 to the detector 420. It should be noted that different arrangements, combinations, and sub-combinations of collimators, mirrors, beamsplitter(s), and/or slits can be employed to direct the beam 410 along a given path based on the dimensions and geometry of the device 400, the overall path-length and width of the beam 410, and the path-length and width of portions of the beam 410 between various collimators, mirrors, beamsplitter(s), and/or slits.

Figure 5:
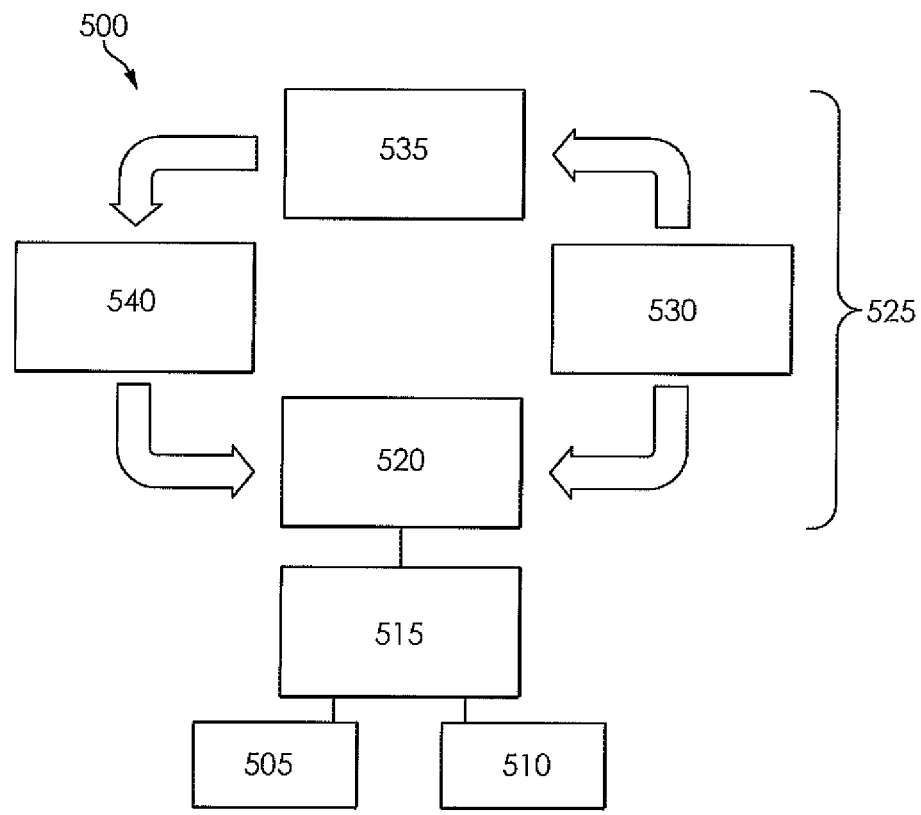
FIG. 5 depicts a schematic for a general thermodynamic refrigeration cycle for temperature control of a detector and an infrared light source.

FIG. 5 depicts an embodiment of a temperature control means including a general thermodynamic refrigeration cycle 500 for a detector 505 and an infrared light source 510 for use in a device (e.g., device 300 in FIG. 3, device 400 in FIG. 4) constructed according to the present technology. The detector 505 and the infrared light source 510 are each thermally coupled to a thermoelectric cooler 515 that includes a heat exchange plate 520. The heat exchange plate 520 is part of a thermodynamic refrigeration cycle 525 including a compressor 530 that compresses a working fluid, a heat exchanger 535 that cools the compressed working fluid, and a conduit 540 such as a copper capillary tube that returns the working fluid to the heat exchange plate 520. The conduit 540 can provide a constriction point in the thermodynamic refrigeration cycle 500 after which the compressed and cooled working fluid can further expand. Expansion of the working fluid draws heat from the detector 505 and the infrared light source 510 through the heat exchange plate 520 of the thermoelectric cooler 515. In this way, the thermoelectric cooler 515 can control the temperature of the infrared light source 510 and can control the temperature of the detector 505, thereby maintaining uniformity in the beam (e.g., beam 310 in FIG. 3, beam 410 in FIG. 4) provided by the infrared light source 510 and in the translation of the infrared light into the electric signal by the detector 505.

Figure 6:
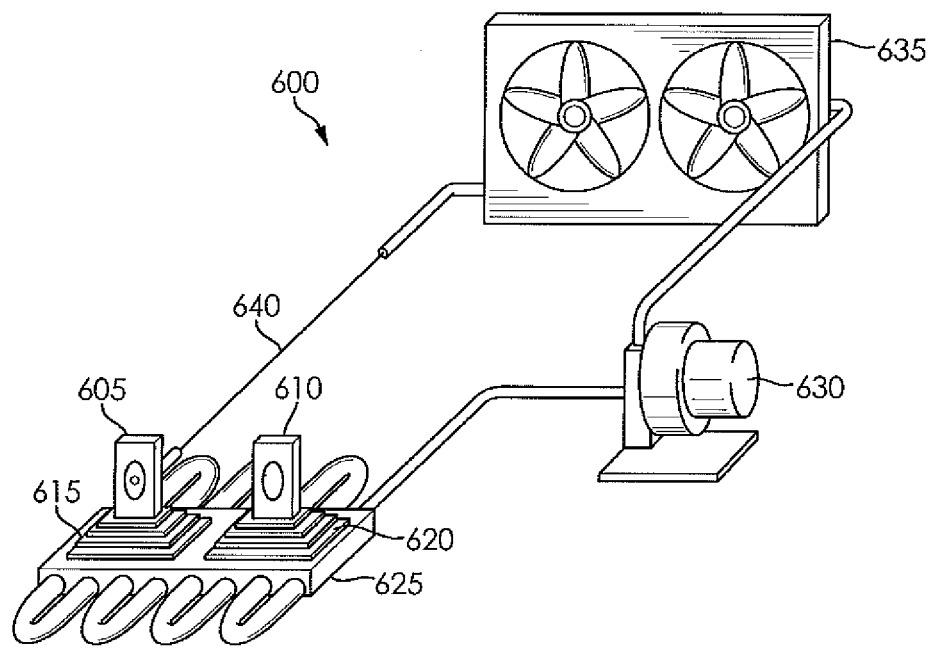
FIG. 6 depicts a schematic for an embodiment of a thermodynamic refrigeration system for a mercury cadmium telluride (MCT) detector and an infrared light emitting diode (IR LED).

FIG. 6 depicts an embodiment of a thermodynamic refrigeration system 600 used as a temperature control means for an MCT detector 605 and an IR LED light source 610 for use in a device (e.g., device 300 in FIG. 3, device 400 in FIG. 4) constructed according to the present technology. The MCT detector 605 is thermally coupled to a first thermoelectric cooler 615 and the IR LED light source 610 is thermally coupled to a second thermoelectric cooler 620. The first thermoelectric cooler 615 and the second thermoelectric cooler 620 are each thermally coupled to a heat exchange plate 625, where the heat exchange plate 625 is part of a thermodynamic refrigeration cycle that includes a compressor 630, a heat exchanger 635, a conduit 640 such as a copper capillary tube. The compressor 630 compresses a working fluid, the heat exchanger 635 cools the compressed working fluid, and the conduit 640 returns the working fluid to the heat exchange plate 625. The conduit 640 can provide a constriction point in the thermodynamic refrigeration system 600 after which the compressed and cooled working fluid can further expand. Expansion of the working fluid draws heat from the MCT detector 605 and the IR LED light source 510 through the heat exchange plate 520 thermally coupled to each thermoelectric cooler 615, 620. In this way, the thermoelectric coolers 615, 620 can control the temperature of the IR LED light source 610 and can control the temperature of the MCT detector 605, respectively, thereby maintaining uniformity in the beam (e.g., beam 310 in FIG. 3, beam 410 in FIG. 4) provided by the IR LED light source 610 and in the translation of the infrared light into the electric signal by the MCT detector 605.

Another embodiment of a temperature control means, not shown, can include a coolant loop fluidly coupled to a heat exchanger. A coolant can be cycled through the coolant loop, where the infrared light source and/or the detector are thermally coupled to the coolant loop. Heat drawn from the infrared light source and/or the detector can be exchanged with ambient air, for example, by passing the coolant through the heat exchanger. The heat exchanger can be configured as a radiator, for example. A pump can be used to cycle the coolant.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A device for detecting an analyte in a liquid, the device comprising: an infrared light source including one of an infrared light emitting diode and a quantum cascade laser, the infrared light source providing a beam having a plurality of infrared wavelengths, the plurality of infrared wavelengths including only a portion of the infrared spectrum, the portion of the infrared spectrum substantially centered on a wavelength absorbable by the analyte, the portion of the infrared spectrum substantially centered on the wavelength absorbable by the analyte limited to a range of wavelengths spanning from about 50 nm to about 150 nm, with about 25 nm to about 75 nm of the range of wavelengths on either side of the wavelength absorbable by the analyte; a liquid positioning means configured to position the liquid so that the beam from the infrared light source passes through the liquid; a detector configured to receive the beam from the infrared light source after the beam passes through the liquid, the detector configured to translate infrared light into an electric signal; a processor configured to transform the electric signal from the detector to an indication of the analyte, the indication of the analyte including a concentration of the analyte with a sensitivity down to 1 ppm; and a temperature control means configured to control a temperature of the infrared light source and a temperature of the detector, thereby maintaining uniformity in the beam provided by the infrared light source and in the translation of the infrared light into the electric signal by the detector.

2. The device of claim 1, wherein the liquid positioning means includes a cuvette with silicon windows.

3. The device of claim 1, wherein the detector includes a mercury cadmium telluride detector.

4. The device of claim 1, wherein the processor employs a Fourier transform process to transform the electric signal from the detector to an indication of the analyte.

5. The device of claim 1, wherein the analyte is fatty acid methyl ester and the infrared light source is configured to provide a beam having a plurality of infrared wavelengths, the plurality of infrared wavelengths including only a portion of the infrared spectrum, the portion of the infrared spectrum substantially centered on a wavelength of about 5.73 μm absorbable by the analyte.

6. The device of claim 1, wherein the temperature control means includes a heat exchanger.

7. The device of claim 1, wherein the liquid positioning means includes a disposable cuvette with silicon windows and the detector includes a mercury cadmium telluride detector.

8. The device of claim 2, wherein the silicon windows have an antireflection coating disposed thereon.

9. The device of claim 1, wherein the liquid positioning means includes a disposable cuvette.

10. A method of detecting an analyte in a liquid, the method comprising: providing a device for detecting the analyte in the liquid, the device including: an infrared light source including one of an infrared light emitting diode and a quantum cascade laser, the infrared light source providing a beam having a plurality of infrared wavelengths, the plurality of infrared wavelengths including only a portion of the infrared spectrum, the portion of the infrared spectrum substantially centered on a wavelength absorbable by the analyte, the portion of the infrared spectrum substantially centered on the wavelength absorbable by the analyte limited to a range of wavelengths spanning from about 50 nm to about 150 nm, with about 25 nm to about 75 nm of the range of wavelengths on either side of the wavelength absorbable by the analyte; a liquid positioning means configured to position the liquid so that the beam from the infrared light source passes through the liquid; a detector configured to receive the beam from the infrared light source after the beam passes through the liquid, the detector configured to translate infrared light into an electric signal; a processor configured to transform the electric signal from the detector to an indication of the analyte; and a temperature control means configured to control a temperature of the infrared light source and a temperature of the detector, thereby maintaining uniformity in the beam provided by the infrared light source and in the translation of the infrared light into the electric signal by the detector generating the beam using the infrared light source; receiving the beam with the detector after the beam passes through the liquid; translating infrared light in the beam received by the detector into an electric signal; and transforming the electric signal from the detector to an indication of the analyte, the indication of the analyte including a concentration of the analyte with a sensitivity down to 1 ppm.

11. A method of detecting an analyte in a liquid, the method comprising: passing a beam through the liquid, the beam provided by an infrared light source, the infrared light source including one of an infrared light emitting diode and a quantum cascade laser, the beam having a plurality of infrared wavelengths, the plurality of infrared wavelengths including only a portion of the infrared spectrum, the portion of the infrared spectrum substantially centered on a wavelength absorbable by the analyte, the portion of the infrared spectrum substantially centered on the wavelength absorbable by the analyte limited to a range of wavelengths spanning from about 50 nm to about 150 nm, with about 25 nm to about 75 nm of the range of wavelengths on either side of the wavelength absorbable by the analyte; receiving the beam with a detector after the beam passes through the liquid; translating infrared light in the beam received by the detector into an electric signal; and transforming the electric signal from the detector to an indication of the analyte, the indication of the analyte including a concentration of the analyte with a sensitivity down to 1 ppm.

12. The method of claim 11, further comprising controlling the temperature of the infrared light source to maintain uniformity in the beam provided by the infrared light source.

13. The method of claim 11, wherein the detector includes a mercury cadmium telluride detector.

14. The method of claim 11, wherein transforming the electric signal from the detector to an indication of the analyte includes using a Fourier transform process.

15. The method of claim 11, wherein the analyte is fatty acid methyl ester and the passing step includes passing a through the liquid, the beam having a plurality of infrared wavelengths, the plurality of infrared wavelengths including only a portion of the infrared spectrum, the portion of the infrared spectrum substantially centered on a wavelength of about 5.73 μm absorbable by the analyte.

16. The method of claim 11, further comprising controlling the temperature of the detector to maintain uniformity in the translation of the infrared light into the electric signal by the detector.

* * * * *